US00PP09618P

United States Patent [19]

Leue

[11] Patent Number: Plant 9,618

[45] Date of Patent: Aug. 6, 1996

[54] IMPATIENS PLANT NAMED 'SPARKLER SALMON'

[75] Inventor: Ellen F. Leue, West Chicago, Ill.

[73] Assignee: Geo. J. Ball, Inc., West Chicago, Ill.

[21] Appl. No.: 445,379

[22] Filed: May 19, 1995

[51] Int. Cl.[6] ..... A01H 5/00

[52] U.S. Cl. ..... Plt./87.6

[58] Field of Search ..... Plt./87.6

*Primary Examiner*—Howard J. Locker

*Attorney, Agent, or Firm*—Burns, Doane, Swecker & Mathis

[57] ABSTRACT

A new and distinct cultivar of Impatiens plant, botanically known as *Impatiens wallerana,* and named 'Sparkler Salmon' is provided. This new cultivar was the result of a controlled breeding program wherein a plant designated 213-1 (non-patented in the United States) was pollinated by a plant designated 43-4-3-1 (non patented in the United States). The new cultivar is early blooming and forms in abundance attractive fully double bicolored blooms that are salmon with irregular streaks of near white. The foliage is medium green. The plant exhibits a good basal-branching character and exhibits a medium upright mounded growth habit.

1 Drawing Sheet

SUMMARY OF THE INVENTION

The present invention provides a new and distinctive Impatiens plant, botanically known as *Impatiens wallerana,* and hereinafter referred to by the cultivar name 'Sparkler Salmon'.

The new cultivar is the product of a planned breeding program. More specifically, the breeding program which resulted in the production of the new cultivar was carried out in a controlled environment during Jun. 1992, at Elburn, Ill., U.S.A. The female parent (i.e., the seed parent) was a plant designated 213-1 (non-patented in the United States) which exhibits pink semi-double flowers and light to medium green foliage. The male parent (i.e., the pollen parent) was a plant designated 43-4-3-1 (non-patented in the United States) which exhibits salmon semi-double flowers with medium green foliage. The parentage of the new cultivar can be summarized as follows:

213-1×43-4-3-1.

The seeds resulting from the above pollination were sown and plantlets were obtained which were physically and biologically different from each other. Selective study resulted in the identification of a single plant of the new cultivar. This plant had distinctive bicolored blooms and initially was designated DP957-1.

It was found that the new cultivar of the present invention:

(a) exhibits in abundance attractive fully double bicolored blooms that are salmon with irregular streaks of near white,
(b) is early blooming,
(c) forms medium green foliage,
(d) exhibits a good basal-branching character, and
(e) exhibits a medium upright mounded growth habit.

Asexual reproduction of the new cultivar by stem cuttings taken during May and Sep., 1993, and during Oct., 1994, by Elburn, Ill., U.S.A. has demonstrated that the characteristics of the new cultivar as herein described are firmly fixed and are retained through successive generations of such asexual propagation.

The 'Sparkler Salmon' cultivar has not been observed under all possible environmental conditions to date. Accordingly, it is possible that the phenotype may vary somewhat with variations in the environment, such as temperature, light intensity, and day length.

The originator is unaware of any commercially available vegetatively-propagated cultivar which is similar to the new 'Sparkler Salmon' cultivar.

when plant material of the 'Sparkler Salmon' cultivar is subjected to standard random amplified polymorphic DNA marker analysis (RAPD) using polymerase chain reaction (PCR) and a known unique set of DNA primers, it is found to exhibit a distinctive fingerprint map which confirms its genetic distinctiveness.

Plants of the new cultivar will be marketed under the FIESTA trademark by Geo. J. Ball, Inc.

BRIEF DESCRIPTION OF THE PHOTOGRAPHS

The accompanying photographs show the new 'Sparkler Salmon' cultivar with colors being as nearly true as it is reasonably possible to make the same in color illustrations of this character. The plants were being grown in greenhouses at West Chicago, Ill., U.S.A.

FIG. 1 — illustrates the general appearance of an overall plant as seen primarily from above.

FIG. 2 — illustrates the general appearance of a typical floret. The blossom coloration is believed to be more accurately depicted in FIG. 2 than in FIG. 1.

DETAILED DESCRIPTION

Figure 1:
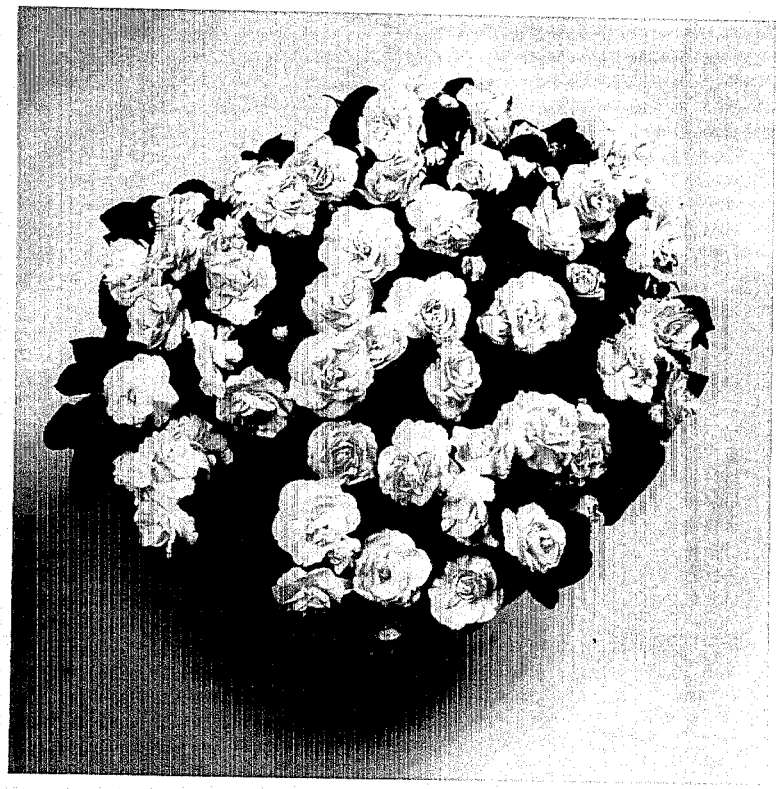
Figure 2:
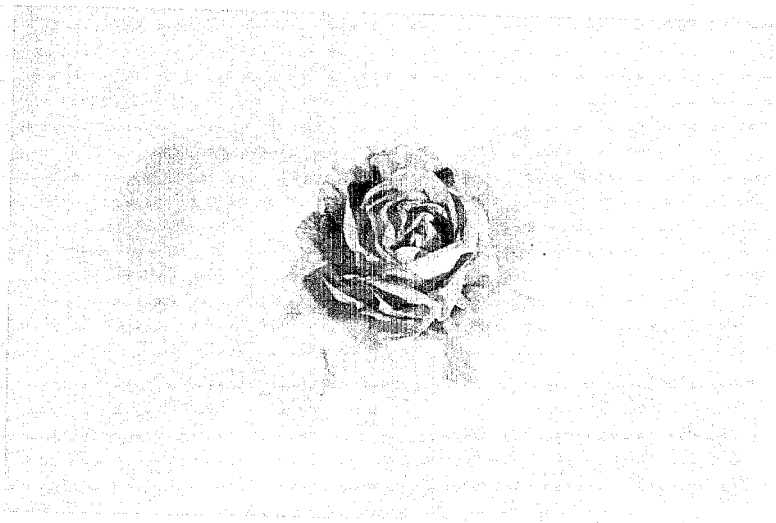

The chart used in the identification of colors described herein is the R.H.S. Colour Chart of The Royal Horticultural Society, London, England. The color values were determined on Jan. 3, 1995. The readings were taken between 10:00 and 11:00 a.m. under 2,000 footcandles of light at West Chicago, Ill., U.S.A. The plants were produced from cuttings taken from stock plants and were grown under greenhouse conditions comparable to those used in commercial practice while utilizing a soilless growth medium and maintaining temperatures of approximately 72° F. during the day and approximately 65° F. during the night.

Propagation:

*Type cutting.*—Two or three vegetative node stem cuttings from near the centers of the plants.

*Time to initiate roots.*—Approximately 7 to 14 days with the shorter times generally being experienced in the summer and the longer times in the winter.

*Rooting habit.*—Fibrous, and branching.

Plant description:

*Habit of growth.*—Basal-branching, and exhibits a medium upright mounded growth habit.

*Form.*—A mature plant at 8 weeks after the planting of a rooted cutting commonly measures approximately 9.0 to 13.0 cm. in height and approximately 19.5 to 23.0 cm. in width.

*Foliage.*—The configuration is ovate with an acuminate tip. The leaves of the new cultivar commonly measure approximately 4.5 to 5.1 cm. in length and approximately 3.5 to 3.7 cm. in width. The foliage of the new cultivar is slightly darker than Green Group 143A (adaxial) and Green Group 143C (abaxial). The stem color is Yellow-Green Group 144C with streaks of Greyed-Purple Group 185A.

Flower description:

*Flowering habit.*—Freely flowering. Small round buds become more oval with maturity and flowers open in a rose-like fashion.

*Natural flowering season.*—Early blooming and blooms throughout the year in a greenhouse environment.

*Flowers borne.*—Slightly above the foliage.

*Flower color.*—Red Group 56A with streaks of Red Group 55C (adaxial) and Red Group 55D (abaxial). The streaks on the adaxial surface are light pink and appear to be nearly white to the eye.

*Quantity of flowers.*—Very floriferous. A mature plant commonly is totally covered with blooms.

*Number of petals.*—Fully double and petals commonly are two numerous to readily count.

*Petal shape.*—Round to oval.

*Flower size.*—Approximately 3.7 to 4.7 cm. in diameter.

*Spur.*—Approximately 3.1 to 3.5 cm. in length.

*Spur color.*—Yellow-Green Group 145C.

*Reproductive organs.*—The stamens are multiple in number and the styles and ovaries are generally typical of the species and non-distinctive.

I claim:

1. A new and distinct cultivar of *Impatiens wallerana* plant named 'Sparkler Salmon' substantially as herein shown and described, which:

(a) exhibits in abundance attractive fully double bicolored blooms that are salmon with irregular streaks of near white,
(b) is early blooming,
(c) forms medium green foliage,
(d) exhibits a good basal-branching character, and
(e) exhibits a medium upright mounded growth habit.

* * * * *